(12) United States Patent
Feroz et al.

(10) Patent No.: US 10,215,705 B2
(45) Date of Patent: Feb. 26, 2019

(54) FIBER OPTIC SYSTEM FOR MEASURING A MULTIPHASE FLOW

(71) Applicant: Petroliam Nasional Berhad, Kuala Lumpur (MY)

(72) Inventors: Sultan @ Maung Maung Myo Thant Feroz, Kajang (MY); Mohd Shahrul Amir S. Zamberi, Kajang (MY); Aida Azni Zulkifli, Kajang (MY); Duhita Sharma, Kajang (MY)

(73) Assignee: Petroliam Nasional Berhad, Kuala Lumpur (MY)

( * ) Notice: Subject to any disclaimer, the term of this patent is extended or adjusted under 35 U.S.C. 154(b) by 0 days.

(21) Appl. No.: 15/608,723

(22) Filed: May 30, 2017

(65) Prior Publication Data

US 2018/0045650 A1 Feb. 15, 2018

Related U.S. Application Data

(62) Division of application No. 13/510,586, filed as application No. PCT/MY2010/000281 on Nov. 15, 2010, now abandoned.

(30) Foreign Application Priority Data

Nov. 19, 2009 (MY) ................................ PI20094923

(51) Int. Cl.
*G01N 21/85* (2006.01)
*G01F 1/74* (2006.01)
*G01F 1/66* (2006.01)

(52) U.S. Cl.
CPC ............. *G01N 21/85* (2013.01); *G01F 1/661* (2013.01); *G01F 1/667* (2013.01); *G01F 1/74* (2013.01)

(58) Field of Classification Search
CPC ......... G01N 21/85; G01F 1/661; G01F 1/667; G01F 1/74
See application file for complete search history.

(56) References Cited

U.S. PATENT DOCUMENTS

| 4,966,462 A * | 10/1990 | Novick | G01F 1/661 356/437 |
| 6,023,340 A * | 2/2000 | Wu | G01F 1/661 356/432 |
| 6,075,611 A * | 6/2000 | Dussan V. | G01F 1/7086 356/432 |
| 2008/0307860 A1* | 12/2008 | Guieze | G01F 1/7086 73/61.44 |
| 2009/0034901 A1* | 2/2009 | Takabayashi | B60K 15/077 385/12 |
| 2009/0216463 A1* | 8/2009 | Xie | G01N 21/314 702/24 |

* cited by examiner

*Primary Examiner* — Violeta A Prieto
(74) *Attorney, Agent, or Firm* — Knobbe Martens Olson & Bear LLP

(57) ABSTRACT

The present invention provides a system for measuring a multiphase flow. Fibre optic probes are arranged around a pipe (109) where a multiphase flow passes through for obtaining information about the flow. The data collected from the probes will be translated into useful information.

23 Claims, 3 Drawing Sheets

FIBER OPTIC SYSTEM FOR MEASURING A MULTIPHASE FLOW

CROSS REFERENCE TO RELATED APPLICATIONS

This application is a divisional of U.S. patent application Ser. No. 13/510,586, filed Sep. 28, 2012, which claims the benefit and priority to and is a U.S. National Phase Application of PCT International Application No. PCT/MY2010/000281, filed on Nov. 15, 2010, designating the United States of America and published in the English language, which is an International Application of and claims the benefit of priority to Malaysian Patent Application No. PI20094923, filed on Nov. 19, 2009. The disclosures of the above-referenced applications are hereby expressly incorporated by reference in their entireties.

FIELD OF THE INVENTION

The present invention relates to a system for measuring a multiphase flow data.

BACKGROUND OF THE INVENTION

Multiphase flows in oil and gas processing are measured typically for obtaining information on phase fraction and flow rate. To obtain such information, flowmeters are used to detect and measure multiphase flows passing through pipes. Different flowmeters incorporate different kinds of sensors or probes for detecting and measuring purposes.

Information on phase faction and phase velocities of a multiphase flow is crucial to well management and optimization of oil & gas production and developments. It is a challenging task to provide accurate measurements of different flow conditions in upstream operation of oil and gas processing. In light of this, flowmeters with sensors and probes that can provide reliable and accurate information are needed.

In order to provide reliable and accurate information during measurement of a multiphase flow, the present invention provides a measurement system using sensitive and reliable sensors so that the system can substantially produce accurate measurement of the multiphase flow.

SUMMARY OF THE INVENTION

In the context of this specification, the term multiphase flow refers to any fluid flow consisting of more than one phase or component. Multiphase flows can be classified according to the state of the different phases or components and therefore refer to gas/solid flows, or liquid/solid flows, or gas/particle flows or bubbly flows and so on.

According to a first embodiment of the present invention, a system for measuring a multiphase flow data using fibre optic sensors or probes is provided. Fibre optic devices such as cables are used for transmitting and detecting optical signals to and from the multiphase flow respectively. The operation of the system will be based on optical reflection and absorption of the multiphase flow.

The sensors or probes will transmit optical signals with different wavelengths from a light source. The signals will be absorbed, diffracted and/or reflected by different phases of the multiphase flow. The amount of lights that are being absorbed, diffracted and/or reflected depend on optical properties of the phases.

The emerging lights coming from the multiphase flow i.e. from absorption, diffraction and/or reflection bears information about the phases. The intensity of the lights will be measured and translated into useful information. For instance, the information includes the distribution of phases contained in the multiphase flow.

An optical multiplexing device, for example, an array waveguide grating (AWG) device is used to multiplex the light source so that the fibre optics carry and transmit different optical wavelengths to the multiphase flow. The number of the sensors or probes can be increased so that more information about the phases can be detected and measured to improve the accuracy of the measurement system.

It is an object of the present invention to provide a system for measuring a multiphase flow data using fibre optic probes that is suitable for producing information regarding the phase fraction and phase velocities of a multiphase flow.

BRIEF DESCRIPTION OF THE INVENTION

The present invention will now be described by way of example, with reference to the accompanying drawings, in which.

DETAILED DESCRIPTION OF THE PRESENT INVENTION

According to a first embodiment of the present invention, a system for measuring a multiphase flow using fibre optic sensors is provided. The system comprises a plurality of fibre optics sensors for transmitting and collecting optical signals to and from the multiphase flow respectively, a multiplexing device for multiplexing optical source into optical signals with different wavelengths, optical circulators for bi-directional transmission of the signals, a filtering device for filtering signals, and an image processing system for processing the collected signals. The processing system includes photodiodes for converting optical signals into electrical signals. The signals will be processed to generate an image representation of the multiphase flow data.

According to the first embodiment, a plurality of fibre optic sensors are arranged around a pipe or tube to detect and measure the multiphase flow that passes through the tube. Preferably the fibre optic sensors are arranged normal to the tube surface. The sensors are arranged at one end to aligned with and to face the corresponding sensors at the other end which is used to collect the transmitted optical signals. In this way, the multiphase flow will flow between the sensors.

The optical source is also referred to as a broadband source. The optical source is produced by a spontaneous emission of an amplified spontaneous emission (ASE) device. Preferably, straight-tipped fibre optics are used and the multiplexing device is an arrayed waveguide grating (AWG) device which multiplexes the optical source and allows multiple wavelengths to be transmitted via individual fibre optic cables.

Figure 1:
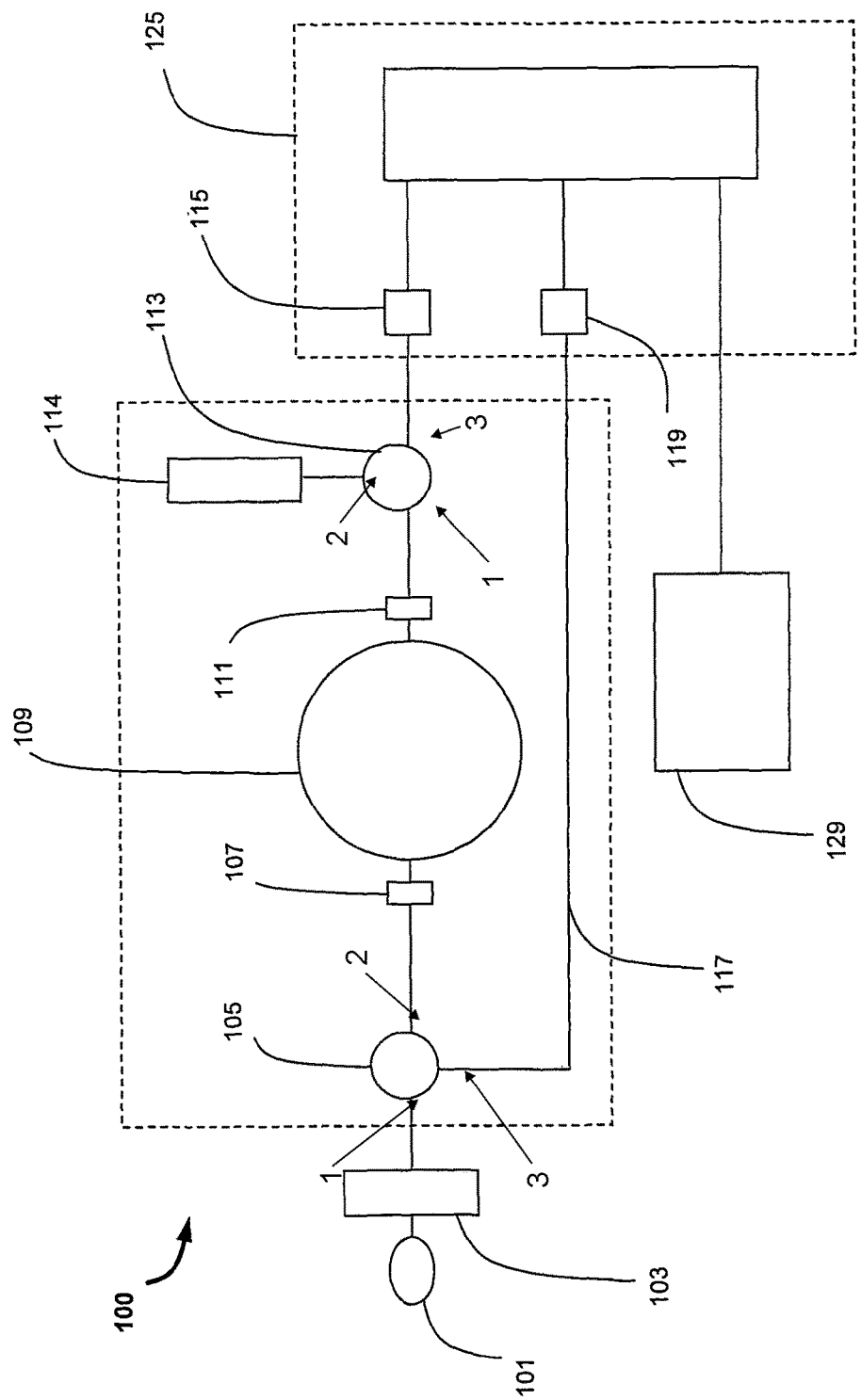
FIG. 1 shows a diagram of a system for measuring a multiphase flow according to a first embodiment of the present invention.

The optical circulator used in the system is a three-port device that allows the optical signals to travel in only one direction—from port 1 to port 2, then from port 2 to port 3. FIG. 1 shows a diagram of the first embodiment. The diagram only illustrates a single fibre optic connection in the system. As shown in FIG. 1, the system 100 comprises an optical source 101, a multiplexing device 103, a first optical circulator 105, a first collimator 107 for collimating and transmitting optical signal, a second collimator 111 for receiving optical signal from the first collimator 107, a filtering device 114 and a second optical circulator 113.

The optical source 101 is connected to the multiplexing device 103 wherein the multiplexing device 103 is connected to the first optical circulator 105 at first port 1 wherein the first optical circulator 105 is connected to the probe via the first collimator 107 via second port 2 of the first optical circulator. Preferably, the first collimator 107 is arranged normal to a pipe or tube 109.

The third port 3 of the first optical circulator 105 is connected to a fibre optic cable (indicated by numeral 117) that allows reflected optical signals from the multiphase flow inside the pipe or tube 109 to be transmitted to the image processing system 1~5 via photodiode 119.

A second collimator 111 of a fibre optic sensor is provided at the other side of the tube 109 which is placed normal to the tube 109 and parallel to the first collimator 107. In the system, the collimators are used to produce collimated optical signals that have parallel wave-fronts. The collimated signals will reduce power loss and noises in the system.

The second collimator 111 is connected to a second optical circulator 113 via the first port 1. The second optical circulator 113 is connected to a filtering device 114 via second port 2. A corresponding photodiode 115 is connected to the second optical circulator 113 via third port 3.

In operation, when the optical signals are transmitted from the first collimator 107 to a multiphase flow which flows in the pipe 109, a portion of the signals will be reflected from the multiphase flow and another portion of the signals will be absorbed and passed through the multiphase flow. The passed through signals will be collected by the second collimator 111. The reflected signals will be directed to an image processing system 125 via third port 3 of the first optical circulator 105. The system includes photodiodes which will convert the optical signals into electrical signals. As shown, the third port 3 is connected to a corresponding photodiode 119. The photodiodes 115 and 119 will convert the optical signals into electrical signals for image processing by the image processing systems 125.

The reflected signals from the multiphase flow provide useful data around the circumference of the pipe 109 whereas the optical signals which pass through the multiphase flow provide data across the flow i.e. cross section or plane information of the flow.

Preferably, the filtering device 114 is a fibre Bragg grating (FBG) device that will filter the signals collected by the corresponding probes. The useful optical signals will directed to the image processing system 125 and be converted into electrical signals via photodiodes. The electrical signals will be further processed by a computer 129 for image reconstruction or tomography. The tomography image produced from the system will provide, for example, intensity distributions of phases contained in a multiphase flow.

According to a second embodiment of the present invention, a system for measuring a multiphase flow using fibre optic probes comprising a plurality of fibre optics for transmitting and collecting optical signals to and from the multiphase flow respectively, a multiplexing device for multiplexing optical source into optical signals with different wavelengths, optical circulators for bidirectional transmission of signals, a filtering device for filtering the signals, photodiodes for converting optical signals into electrical signals, and an image processing system for processing the collected signals. The system further comprises an optical amplifier for amplifying the optical signals, and an optical splitter for splitting the amplified optical signals.

Figure 2:
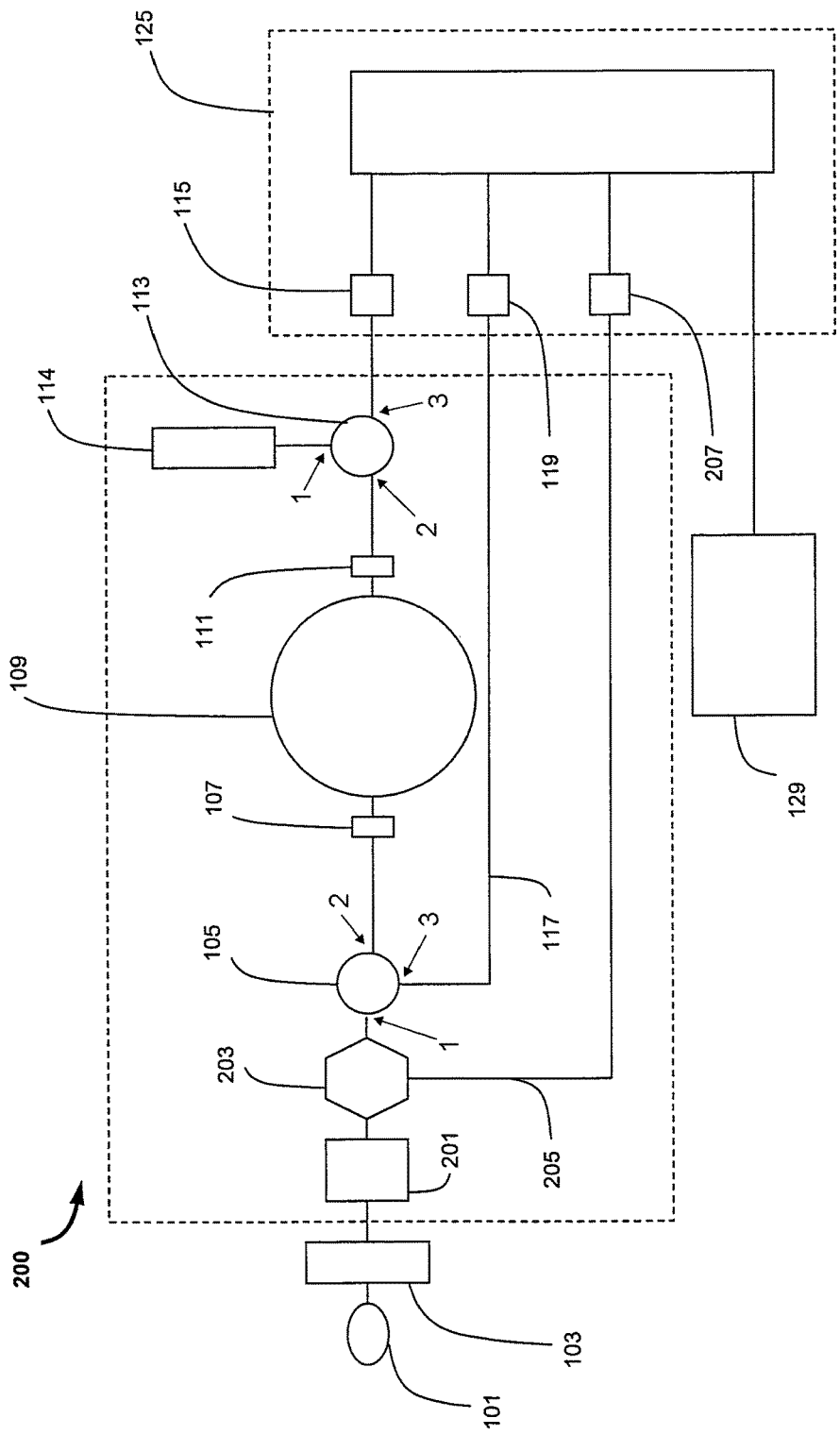
FIG. 2 shows-a diagram of a system for measuring a multiphase flow according to a second embodiment of the present invention.

FIG. 2 shows a diagram of the second embodiment. As shown in FIG. 2, optical signals from the AWG device 103 will be amplified by an optical amplifier 201. The amplified signals will be then split by an optical splitter 203 into two portions of signals which are transmission signals and reference signals. A large portion, for example 99% of the amplified signals is split into the transmission signals and a small portion of 1% is split into the reference signals. The reference signals indicated by numeral 205 will be directed to the image processing system 125 via a corresponding photodiode 207 which in turn converting the signals into electrical signals for reference data of the system. The transmission signals will be directed to the first optical circulator 105. The first optical circulator 105 is connected to fibre optic probe via the first collimator 107. From this point forward the system of the second embodiment is arranged as depicted in FIG. 1.

Figure 3:
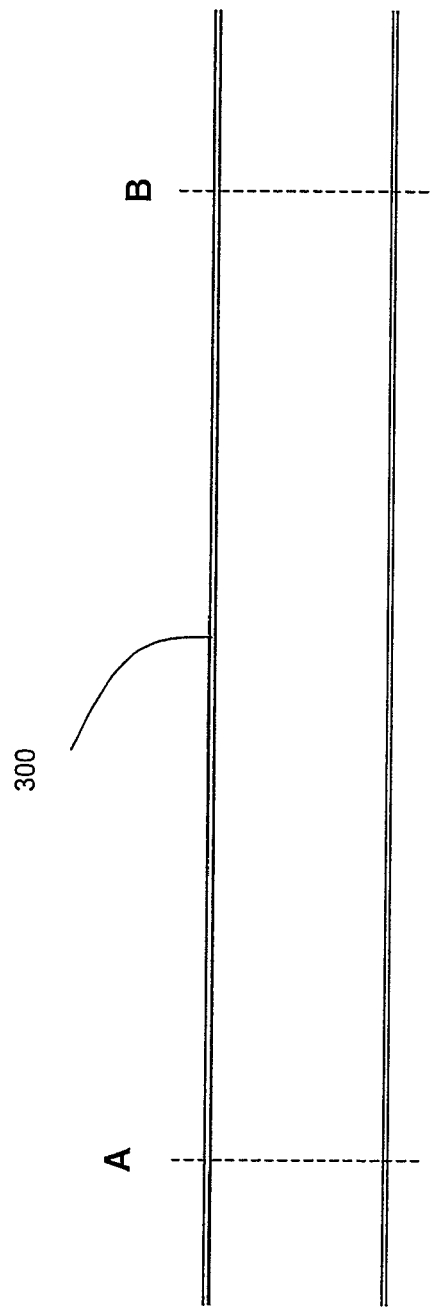
FIG. 3 shows an arrangement of the system for measuring phase velocity.

The system either the first or second embodiment can be arranged at two different locations along the pipe 109 for measuring velocity of the multiphase flow. As shown in FIG. 3, two systems are distance apart from one another at location A and location B. For instance, time taken for a multiphase flow to travel from A to B will provide information on velocity or flow rate.

The system according to present invention can be used as independent flowmeter or be incorporated to other flowmeter as an additional measuring system.

The invention claimed is:

1. A system for measuring a multiphase flow comprising:
   an optical source connected to a multiplexer for multiplexing the optical source into optical signals with different wavelengths for transmission into the multiphase flow;
   at least a first fiber optic probe connected to the multiplexer, the first probe for transmitting the optical signals from the multiplexer into the multiphase flow, collecting reflected signals from the multiphase flow, and directing them to a first photodiode;
   at least a second fiber optic probe for collecting optical signals passing through the multiphase flow;
   a filter connected to the second probe capable of filtering the signals passing through the multiphase flow; and
   a second photodiode for collecting optical signals from the filter, wherein the first and second photodiodes convert the collected optical signals into electrical signals that are used by a computer to develop an image representation of the multiphase flow.

2. The system for measuring a multiphase flow according to claim 1, wherein the computer is capable of displaying a tomography image representation of the multiphase flow.

3. The system for measuring a multiphase flow according to claim 1, wherein the fiber optic probes are arranged around a pipe where the multiphase flow passes through.

4. The system for measuring a multiphase flow according to claim 1, wherein the first fiber optic probe is arranged to align with and face the second fiber optic probe.

5. The system for measuring a multiphase flow according to claim 1, wherein each of the fiber optic probes includes a collimator positioned normal to a pipe surface.

6. The system for measuring a multiphase flow according to claim 1, further comprising an optical source directed to the multiplexer.

7. The system for measuring a multiphase flow according to claim 1, wherein the multiplexer is connected to a first optical circulator via a first port of the first optical circulator.

8. The system for measuring a multiphase flow according to claim 7, wherein the first optical circulator is connected to the first fiber optic probe via a second port of the first optical circulator.

9. The system for measuring a multiphase flow according to claim 8, wherein the first optical circulator is connected to the first photodiode via a third port of the first optical circulator.

10. The system for measuring a multiphase flow according to claim 7, wherein the second fiber optic probe is connected to a second optical circulator via a first port of the second optical circulator for directing optical signals to the filter connected at a second port of the second optical circulator.

11. The system for measuring a multiphase flow according to claim 10, wherein the optical signals reflected from the filtering device are directed to the second photodiode via a third port of the second optical circulator.

12. The system for measuring a multiphase flow data according to claim 1, wherein the system further comprises at least one optical amplifier and at least one optical splitter connected to the multiplexer, the amplifier for amplifying the optical signals output from the multiplexer and the at least one optical splitter for splitting the amplified optical signals into transmission signals and reference signals.

13. The system for measuring a multiphase flow according to claim 12, wherein the optical amplifier is connected to the optical splitter.

14. The system for measuring a multiphase flow according to claim 12, further comprising an optical source directed to the multiplexer.

15. The system for measuring a multiphase flow according to claim 12, wherein the multiplexer is connected to the optical amplifier.

16. The system for measuring a multiphase flow according to claim 12, wherein the at least one optical splitter is connected to a first optical circulator via a first port of the first optical circulator for directing a first portion of the signals.

17. The system for measuring a multiphase flow according to claim 12, wherein the reference signal is directed to a third photodiode for converting the optical reference signals into electrical signals for reference data of the system.

18. The system for measuring a multiphase flow, according to claim 16, wherein the first optical circulator is connected to the first fiber optic probe via a second port of the first optical circulator.

19. The system for measuring a multiphase flow according to claim 17, wherein the first optical circulator is connected to the third photodiode via a third port of the first optical circulator.

20. The system for measuring a multiphase flow according to claim 1, wherein the multiplexer is an arrayed waveguide grating device.

21. The system for measuring a multiphase flow according to claim 1, wherein the filter is a fiber Bragg grating device.

22. A system for measuring a multiphase flow according to claim 6, wherein the optical source is an amplified spontaneous emission broadband light.

23. A system for measuring a multiphase flow comprising, at least two systems according to claim 1, wherein the systems are placed at two different locations along a pipe for measuring velocity of a flow through the pipe.

* * * * *